United States Patent
Han et al.

(10) Patent No.: US 11,703,497 B1
(45) Date of Patent: Jul. 18, 2023

(54) QUANTITATIVE EVALUATION METHOD FOR SENSITIVITY OF WELDING TRANSVERSE COLD CRACKS IN TYPICAL JOINT OF JACKET

(71) Applicant: Tianjin University, Tianjin (CN)

(72) Inventors: Yongdian Han, Tianjin (CN); Shifang Zhong, Tianjin (CN); Lianyong Xu, Tianjin (CN); Hongyang Jing, Tianjin (CN); Lei Zhao, Tianjin (CN); Kangda Hao, Tianjin (CN)

(73) Assignee: Tianjin University, Tianjin (CN)

( * ) Notice: Subject to any disclaimer, the term of this patent is extended or adjusted under 35 U.S.C. 154(b) by 0 days.

(21) Appl. No.: 17/954,682

(22) Filed: Sep. 28, 2022

(30) Foreign Application Priority Data

Jan. 20, 2022 (CN) .......................... 202210067444.1

(51) Int. Cl.
| | |
|---|---|
| G01N 1/28 | (2006.01) |
| G01N 3/02 | (2006.01) |
| G01N 3/06 | (2006.01) |
| G01N 21/88 | (2006.01) |
| G01N 23/04 | (2018.01) |
| G01N 30/02 | (2006.01) |
| G01N 30/06 | (2006.01) |
| G01N 33/207 | (2019.01) |
| G01N 30/62 | (2006.01) |
| B23K 31/12 | (2006.01) |
| G01N 33/2045 | (2019.01) |

(52) U.S. Cl.
CPC ......... *G01N 33/207* (2019.01); *B23K 31/125* (2013.01); *G01N 30/62* (2013.01); *G01N 33/2045* (2019.01); *G01N 2030/027* (2013.01)

(58) Field of Classification Search
None
See application file for complete search history.

(56) References Cited

FOREIGN PATENT DOCUMENTS

| CN | 105945443 A | * | 9/2016 | ........... B23K 31/125 |
|---|---|---|---|---|
| CN | 106735996 A | * | 5/2017 | ........... B23K 31/125 |

(Continued)

*Primary Examiner* — Daniel S Larkin

(57) ABSTRACT

The present invention discloses a quantitative evaluation method for sensitivity of welding transverse cold cracks in a typical joint of a jacket, including following steps: S1, performing macroscopic analysis, metallographic analysis, fracture analysis and hardness analysis on cracks of a failed component to obtain main causes of cold crack failure; and S2, designing and processing a dedicated sample, and performing rigid restraint crack tests on the dedicated sample at different preheating temperatures to obtain a cracking/non-cracking critical restraint stress $\sigma 1cr$ of the sample. According to the method, a rigid restraint crack test is applied to evaluation of sensitivity of welding transverse cracks, so that external restraint conditions borne by a welding joint can be accurately simulated, a stress state of the welding joint in an actual working condition can be truly reflected, the overall evaluation precision is greatly improved, and a foundation is laid for accurately evaluating sensitivity of welding cold cracks in a tube joint. Furthermore, a welding technology (base material, welding material, welding process and restraint level) is designed to restrain cold cracks from cracking, and the method has important theoretical significance and engineering value.

7 Claims, 1 Drawing Sheet

(56) References Cited

FOREIGN PATENT DOCUMENTS

| CN | 112067781 A | * | 12/2020 | ............. G01N 27/84 |
| CN | 112775579 A | * | 5/2021 | ........... B23K 31/125 |
| KR | 20110077051 A | * | 7/2011 | ............... G01N 1/28 |

* cited by examiner

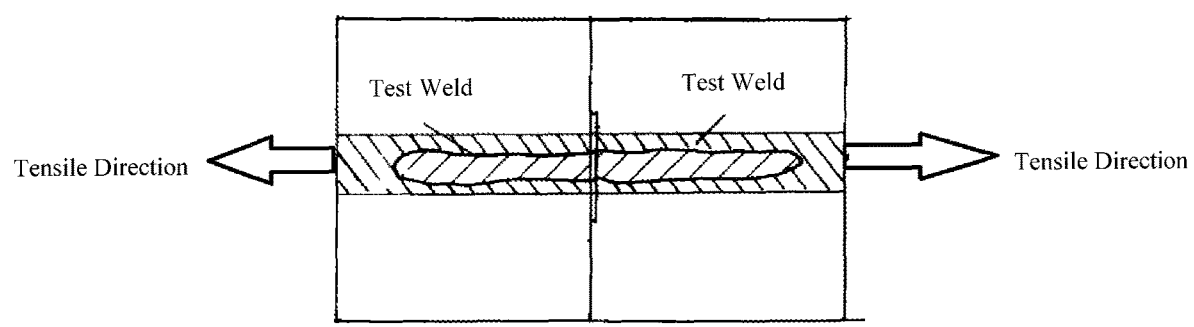

QUANTITATIVE EVALUATION METHOD FOR SENSITIVITY OF WELDING TRANSVERSE COLD CRACKS IN TYPICAL JOINT OF JACKET

TECHNICAL FIELD

The present invention belongs to the technical field of welding cracks, and particularly relates to a quantitative evaluation method for sensitivity of welding transverse cold cracks in a typical joint of a jacket.

BACKGROUND

Although high-strength steel is widely used in offshore jacket structures, its cold crack problem in welding construction is more prominent, and a damage caused by the lag of cold cracks in tube joints is also very serious. At present, there are many methods for evaluating sensitivity of longitudinal cold cracks in welds and heat-affected zones, and they are relatively complete. However, there are relatively few evaluation methods for welding transverse cracks, and they have their own limitations, that is, a restraint intensity is fixed and is not adjustable, so it is impossible to compare the advantages and disadvantages of welding materials or welding processes that have cracks at the same time after welding.

In addition, because an existing evaluation method for welding transverse cracks is fixed and strict in restraint intensity, a stress state after welding cannot reach the same level as that of an actual engineering structure, which makes the existing evaluation method unable to truly evaluate sensitivity of transverse cracks in actual engineering, thus, it is easy to cause a problem that when a large number of transverse cracks appear in crossing-line welds of a K/T/Y tube joint of an offshore platform structure jacket, there is no suitable method for accurate evaluation.

Therefore, aiming at the above technical problem, it is necessary to provide a quantitative evaluation method for sensitivity of welding transverse cold cracks in a typical joint of a jacket.

SUMMARY

In order to accurately evaluate sensitivity of welding cold cracks in a tube joint, and then design a welding technology to restrain transverse cold cracks from cracking, the present invention proposes a quantitative evaluation method for sensitivity of welding cold cracks in a typical joint of a jacket based on an analysis of causes of cold crack of a failed component, a welding cold crack test (rigid restraint crack test) and a finite element numerical simulation analysis, and proposes a measure for effectively restraining cold cracks based on a relationship between the sensitivity of transverse cold cracks obtained by means of this method and a cracking mechanism.

In order to achieve the above object, an embodiment of the present invention provides the following technical scheme.

A quantitative evaluation method for sensitivity of welding transverse cold cracks in a typical joint of a jacket, including following steps:

S1. Performing macroscopic analysis, metallographic analysis, fracture analysis and hardness analysis on cracks of a failed component to obtain main causes of cold crack failure;

S2. Designing and processing a dedicated sample, and performing rigid restraint crack tests on the dedicated sample at different preheating temperatures to obtain a cracking/non-cracking critical restraint stress $\sigma 1cr$ of the sample;

S3. Measuring diffusion hydrogen contents of the sample in the rigid restraint crack tests at different preheating temperatures;

S4. Fitting the critical restraint stress $\sigma 1cr$ obtained in S2 with the diffusion hydrogen contents measured in S3 to obtain a critical cracking equation of transverse cold cracks in welds;

S5. Performing numerical simulation calculation on a welding restraint stress of the typical joint of the jacket, and analyzing a restraint stress and a diffusion hydrogen content at a dangerous point of a tube joint;

S6. Quantitatively evaluating sensitivity of welding cold cracks in the typical joint of the jacket by combining the restraint stress and the diffusion hydrogen content at the dangerous point which are obtained from numerical simulation, and the critical cracking equation obtained from rigid restraint crack tests; and S7. Based on a failure analysis, the critical cracking equation obtained from the rigid restraint crack tests, and a numerical simulation analysis result, proposing an effective measure for restraining welding transverse cold cracks, to provide relevant basis for a welding design of the typical joint of the jacket.

Further, pre-welding treatment is required to be performed on the dedicated sample in S2, the pre-welding treatment including: cleaning groove burrs, and removing oil stains on a groove surface by means of alcohol or acetone.

Further, the dedicated sample has a groove of 30°, a root face of 1 mm, and a root gap of 2 mm during welding.

Further, the groove burrs are cleaned by a steel file or a grinding wheel and ground by a grinder until metallic luster is exposed, and a time duration for removing the oil stains on the groove surface is 2-3 h.

Further, a weld direction of the dedicated sample in S2 is consistent with a stress direction, can generate welding transverse cracks, and is suitable for rigid restraint crack tests.

Further, the rigid restraint crack tests in S2 are realized by a rigid adjustable restraint tester, that is, the dedicated sample is fixed onto the rigid adjustable restraint tester, welding is performed under a restraint condition, so that a restraint stress keeps a load for 48 h, multiple groups of tests are repeated, and a restraint intensity of the sample is continuously adjusted to obtain a cracking/non-cracking critical restraint stress.

Further, the diffusion hydrogen contents in S3 are measured by gas chromatography, multiple measurements are required to be performed in each group of tests, and an average value of multiple measurement results is taken.

Further, the critical cracking equation of the transverse cold cracks in the welds in S4 is utilized to calculate a critical diffusion hydrogen content to avoid cold cracks under a certain stress and a critical stress to avoid cold cracks under a certain weld diffusion hydrogen content.

Further, in the numerical simulation in S5, an actual welding procedure is simulated according to an actual welding process, a stress field and a diffusion hydrogen content after welding are calculated, and a restraint stress and a diffusion hydrogen content at a dangerous point are obtained through analysis and comparison.

Further, the effective measure for restraining welding transverse cold cracks in S7 includes regulating a restraint level of an actual engineering structure, diffusion hydrogen contents of a base material and a welding material, and optimizing welding process.

Compared with the existing technology, the present invention has the following advantages:

According to the method, a rigid restraint crack test is applied to evaluation of sensitivity of welding transverse cracks, so that external restraint conditions borne by a welding joint can be accurately simulated, a stress state of the welding joint in an actual working condition can be truly reflected, the overall evaluation precision is greatly improved, and a foundation is laid for accurately evaluating sensitivity of welding cold cracks in a tube joint. Furthermore, a welding technology (base material, welding material, welding process and restraint level) is designed to restrain cold cracks from cracking, and the method has important theoretical significance and engineering value.

BRIEF DESCRIPTION OF DRAWINGS

In order to more clearly describe the technical scheme in the embodiments of the present invention or in the existing technology, the drawing required to be used in the description of the embodiments or the existing technology will be simply presented below. Apparently, the drawing in the following description is merely one embodiment of the present invention, and for those having ordinary skill in the art, other drawings can also be obtained according to the provided drawing without contributing creative labor.

FIG. 1 is a schematic diagram of a dedicated sample of transverse cracks generated in an embodiment of the present invention.

DETAILED DESCRIPTION

The present invention will be described in detail below with reference to the embodiments shown in the drawing. However, these embodiments are not intended to limit the present invention, and the structural, method or functional changes made by those having ordinary skill in the art according to these embodiments are all included in the protection scope of the present invention.

The present invention discloses a quantitative evaluation method for sensitivity of welding transverse cold cracks in a typical joint of a jacket, as shown in FIG. 1, including following steps:

In a step of S1, macroscopic analysis, metallographic analysis, fracture analysis and hardness analysis are performed on cracks of a failed component to obtain main causes of cold crack failure;

In a step of S2, a dedicated sample is designed and processed, and rigid restraint crack tests are performed on the dedicated sample at different preheating temperatures to obtain a cracking/non-cracking critical restraint stress $\sigma 1cr$ of the sample;

In a step of S3, diffusion hydrogen contents of the sample in the rigid restraint crack tests at different preheating temperatures are measured;

In a step of S4, the critical restraint stress $\sigma 1cr$ obtained in S2 is fitted with the diffusion hydrogen contents measured in S3 to obtain a critical cracking equation of transverse cold cracks in welds;

In a step of S5, numerical simulation calculation is performed on a welding restraint stress of the typical joint of the jacket, and a restraint stress and a diffusion hydrogen content at a dangerous point of a tube joint are analyzed;

In a step of S6, sensitivity of welding cold cracks in the typical joint of the jacket is quantitatively evaluated by combining the restraint stress and the diffusion hydrogen content at the dangerous point which are obtained from numerical simulation, and the critical cracking equation obtained from rigid restraint crack tests; and In a step of S7, based on a failure analysis, the critical cracking equation obtained from the rigid restraint crack tests, and a numerical simulation analysis result, an effective measure for restraining welding transverse cold cracks is proposed, to provide relevant basis for a welding design of the typical joint of the jacket.

In this embodiment, the macroscopic analysis in S1 is utilized to check whether there are cracks in the failed component. Besides direct visual inspection and tapping sound measurement, cracks can also be detected by a nondestructive inspection method. When cracks are extremely small, the presence of micro-cracks can also be detected by means of an optical microscope and an electronic microscope.

Pre-welding treatment is required to be performed on the dedicated sample in S2, the pre-welding treatment including: cleaning groove burrs, and removing oil stains on a groove surface by means of alcohol or acetone.

In addition, the dedicated sample has a groove of 30°, a root face of 1 mm, and a root gap of 2 mm during welding; and the groove burrs are cleaned by a steel file or a grinding wheel and ground by a grinder until metallic luster is exposed, and a time duration for removing the oil stains on the groove surface is 2-3 h.

In one embodiment, a weld direction of the dedicated sample in S2 is consistent with a stress direction, can generate welding transverse cracks, and is suitable for rigid restraint crack tests.

In addition, the rigid restraint crack tests in S2 are realized by a rigid adjustable restraint tester, that is, the dedicated sample is fixed onto the rigid adjustable restraint tester, welding is performed under a restraint condition, so that a restraint stress keeps a load for 48 h, multiple groups of tests are repeated, and a restraint intensity of the sample is continuously adjusted to obtain a cracking/non-cracking critical restraint stress.

In this embodiment, the diffusion hydrogen contents in S3 are measured by gas chromatography, multiple measurements are required to be performed in each group of tests, and an average value is taken under the condition that test data is correct in order to reduce test errors.

When measuring the diffusion hydrogen contents by gas chromatography, hydrogen accumulation treatment is required to be performed, that is, a collector containing the sample is required to be placed in a thermostat of (45+/−1°) C. and stored for 72 h until diffusion hydrogen is completely collected.

In addition, in gas chromatography, activation treatment is required to be performed, and a stationary phase is required to be filled with a molecular sieve solid adsorbent of 30-40 meshes, which is mainly utilized for analysis of inert gases, $H_2$, $O_2$, $N_2$, $CO_2$, $CH_4$ and other common gases and organic substances with low boiling point.

In one embodiment, the activation treatment method includes crushing, sieving and baking at 550-600° C. for 4 h.

In this embodiment, the critical cracking equation of the transverse cold cracks in the welds in S4 is utilized to calculate a critical diffusion hydrogen content to avoid cold cracks under a certain stress and a critical stress to avoid cold cracks under a certain weld diffusion hydrogen content.

The critical cracking equation of the transverse cold cracks of the weld is: $\sigma_{1cr}+120 \times \ln H=546.8$, where $\sigma_{1cr}$ represents the critical restraint stress, and H represents the diffusion hydrogen contents, that is, on the basis of a gapped bead-on-plate (G-BOP) test, the critical cracking equation of the transverse cold cracks in the welds is obtained through regression analysis by adjusting a dew point of a protective gas, changing the weld diffusion hydrogen content and measuring different critical preheating temperatures of the welds.

In one embodiment, methods and steps for obtaining the critical cracking equation of the transverse cold cracks in the welds are in the existing technology, which will not be repeated here.

In this embodiment, in the numerical simulation in S5, an actual welding procedure is simulated according to an actual welding process, a stress field and a diffusion hydrogen content after welding are calculated, and a restraint stress and a diffusion hydrogen content at a dangerous point are obtained through analysis and comparison.

The welding process includes the following steps.

In a step of S501, a dedicated sample of a rigid restraint cold cracking machine is machined by mechanical processing.

In a step of S502, test plates are installed on the rigid restraint cold cracking machine and assembled and butted in pairs, rust, oil stains, oxide scale, etc. on a surface of a middle part to be welded are cleaned with a grinding wheel and a wire brush and scrubbed with alcohol, an extensometer is installed, a restraint distance is determined, and a level is ensured.

In a step of S503, an induction preheating device is prepared and a preheating temperature (66° C.) is set before welding, and thermocouples for temperature measurement are installed on the back of each of the test plates and are located 25 mm on both sides of the groove.

In a step of S504, an appropriate welding process is selected, and a welding heat input, a welding wire and a protective gas are determined. A DW-A55L welding wire and a mixed gas of 20% Ar+80% CO2 as a protective gas are selected for welding.

In a step of S505, after welding, the test plates are placed at a room temperature for 48 h, to observe whether the test plates break or crack within 48 h, and corresponding restraint intensities are recorded.

In this embodiment, the effective measure for restraining welding transverse cold cracks in S7 includes regulating a restraint level of an actual engineering structure, diffusion hydrogen contents of a base material and a welding material, and optimizing welding process.

Optimizing welding process may be realized by changing a preheating condition and a welding heat input.

It is apparent to those having ordinary skill in the art that the present invention is not limited to details of the above demonstrative embodiments. Moreover, the present invention can be implemented in other specific forms without departing from the spirit or basic feature of the present invention. Therefore, in all respects, the embodiments shall be regarded to be demonstrative and nonrestrictive. The scope of the present invention is defined by appended claims, rather than the above description. Therefore, the present invention is intended to include all changes falling into the meaning and the scope of equivalent elements of the claims within the present invention. Any reference numeral in the claims shall not be regarded to limit the concerned claims.

In addition, it shall be understood that although this description is explained in accordance with the embodiments, not every embodiment only includes one independent technical scheme. This narration mode of the description is only for clarity. Those having ordinary skill in the art shall regard the description as a whole, and the technical schemes in various embodiments can also be appropriately combined to form other embodiments understandable for those having ordinary skill in the art.

The invention claimed is:

1. A quantitative evaluation method for determining a sensitivity of a weld in a joint of a jacket to develop a transverse cold crack, characterized by comprising following steps:
    S1, performing visual inspection, metallographic analysis, fracture analysis and hardness analysis on cracks of a failed component to obtain a cause of cold crack failure;
    S2, obtaining a sample, and performing rigid restraint crack tests through a rigid adjustable restraint tester on the sample at different preheating temperatures to obtain a cracking/non-cracking critical restraint stress $\sigma_{1cr}$ of the sample;
    S3, measuring diffusion hydrogen contents of the sample in the rigid restraint crack tests at different preheating temperatures;
    S4, fitting the critical restraint stress $\sigma_{1cr}$ obtained in S2 with the diffusion hydrogen contents measured in S3 to obtain a critical cracking equation of transverse cold cracks in welds;
    S5, performing numerical simulation calculation on a welding restraint stress of the joint of the jacket, and analyzing a restraint stress and a diffusion hydrogen content at the weld in the joint of the jacket;
    S6, quantitatively evaluating the sensitivity of the weld in the joint of the jacket by combining the restraint stress and the diffusion hydrogen content at the weld which are obtained from numerical simulation, and the critical cracking equation obtained from rigid restraint crack tests;
    S7, based on a failure analysis, the critical cracking equation obtained from the rigid restraint crack tests, and a numerical simulation analysis result, proposing an effective measure for restraining the weld in the joint of the jacket to develop the transverse cold crack, to provide relevant basis for a welding design of the joint of the jacket;
    wherein the critical cracking equation of the transverse cold cracks of the weld is: $\sigma_{1cr}+120 \times \ln H=546.8$, where, on the basis of a gapped bead-on-plate (G-BOP) test, the critical cracking equation of the transverse cold cracks in the welds is obtained through regression analysis by adjusting a dew point of a protective gas, changing the weld diffusion hydrogen content and measuring different critical preheating temperatures of the welds, where the protective gas is a mixed gas consisting of 20% Ar and 80% $CO_2$;
    the effective measure for restraining the weld in the joint of the jacket to develop the transverse cold crack in S7 comprises regulating diffusion hydrogen contents of a welding material of the weld;
    in the numerical simulation in S5, a stress field and a diffusion hydrogen content after welding are calculated, and the restraint stress and the diffusion hydrogen content at the weld are obtained through analysis.

2. The quantitative evaluation method for determining a sensitivity of a weld in a joint of a jacket to develop a transverse cold crack of claim 1, characterized in that a pre-welding treatment is required to be performed on the sample in S2, the pre-welding treatment including: cleaning groove burrs, and removing oil stains on a groove surface by means of alcohol or acetone.

3. The quantitative evaluation method for determining a sensitivity of a weld in a joint of a jacket to develop a transverse cold crack of claim 2, characterized in that the sample has a groove of 30°, a root face of 1 mm, and a root gap of 2 mm during welding.

4. The quantitative evaluation method for determining a sensitivity of a weld in a joint of a jacket to develop a transverse cold crack of claim 2, characterized in that the groove burrs are cleaned by a steel file or a grinding wheel and ground by a grinder until metallic luster is exposed, and a time duration for removing the oil stains on the groove surface is 2-3 h.

5. The quantitative evaluation method for determining a sensitivity of a weld in a joint of a jacket to develop a transverse cold crack of claim 1, characterized in that the rigid restraint crack tests in S2 are realized by a rigid adjustable restraint tester, the sample is fixed onto the rigid adjustable restraint tester, and welding is performed under a restraint condition, so that a restraint stress keeps a load for 48 h, multiple groups of tests are repeated, and a restraint intensity of the sample is continuously adjusted to obtain a cracking/non-cracking critical restraint stress.

6. The quantitative evaluation method for determining a sensitivity of a weld in a joint of a jacket to develop a transverse cold crack of claim 1, characterized in that the diffusion hydrogen contents in S3 are measured by gas chromatography, multiple measurements are required to be performed in each group of tests for measuring the diffusion hydrogen contents in S3, and an average value of multiple measurement results corresponding to the multiple measurements is taken.

7. The quantitative evaluation method for determining a sensitivity of a weld in a joint of a jacket to develop a transverse cold crack of claim 1, characterized in that the critical cracking equation of the transverse cold cracks in the welds in S4 is utilized to calculate a critical diffusion hydrogen content to avoid cold cracks under a certain stress and a critical stress to avoid cold cracks under a certain weld diffusion hydrogen content.

* * * * *